US008765881B2

(12) United States Patent
Hays et al.

(10) Patent No.: US 8,765,881 B2
(45) Date of Patent: Jul. 1, 2014

(54) METHODS OF MAKING POLYDIORGANOSILOXANE POLYOXAMIDE COPOLYMERS

(75) Inventors: David S. Hays, Woodbury, MN (US); Richard G. Hansen, Mahtomedi, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 13/514,497

(22) PCT Filed: Dec. 22, 2010

(86) PCT No.: PCT/US2010/061817
§ 371 (c)(1),
(2), (4) Date: Jun. 7, 2012

(87) PCT Pub. No.: WO2011/082069
PCT Pub. Date: Jul. 7, 2011

(65) Prior Publication Data
US 2012/0271025 A1    Oct. 25, 2012

Related U.S. Application Data

(60) Provisional application No. 61/291,008, filed on Dec. 30, 2009.

(51) Int. Cl.
C08G 77/452    (2006.01)
C08G 77/26     (2006.01)
C07C 69/34     (2006.01)
C07C 55/06     (2006.01)

(52) U.S. Cl.
CPC .............. *C08G 77/452* (2013.01); *C07C 69/34* (2013.01)
USPC ........................................................ 525/474

(58) Field of Classification Search
CPC ............................... C08G 77/452; C07C 69/34
USPC ........................................................ 525/474
See application file for complete search history.

(56) References Cited

U.S. PATENT DOCUMENTS

| 2,343,808 A | 3/1944 | Schlack |
| 3,250,807 A | 5/1966 | Fritz |
| 3,392,097 A | 7/1968 | Gozzo |
| 3,400,080 A * | 9/1968 | Maulding ................... 252/700 |
| 3,442,815 A * | 5/1969 | Laszlo et al. ................ 252/700 |
| 3,442,942 A | 5/1969 | Sianesi |
| 3,485,806 A | 12/1969 | Bloomquist |
| 3,553,289 A * | 1/1971 | Duxbury et al. ............... 25/432 |
| 3,699,145 A | 10/1972 | Sianesi |
| 3,715,378 A | 2/1973 | Sianesi |
| 3,728,311 A | 4/1973 | Park |
| 3,810,874 A | 5/1974 | Mitsch |
| 3,890,269 A | 6/1975 | Martin |
| 4,085,137 A | 4/1978 | Mitsch |
| 4,119,615 A * | 10/1978 | Schulze ........................ 528/343 |
| 4,178,432 A * | 12/1979 | Chen et al. .................... 528/340 |
| 4,661,577 A | 4/1987 | Jo Lane |
| 4,684,728 A | 8/1987 | Möhring |
| 5,026,890 A | 6/1991 | Webb |
| 5,093,432 A | 3/1992 | Bierschenk |
| 5,214,119 A | 5/1993 | Leihr |
| 5,266,650 A | 11/1993 | Guerra |
| 5,276,122 A | 1/1994 | Aoki |
| 5,461,134 A | 10/1995 | Leir |
| 5,488,142 A | 1/1996 | Fall |
| 5,512,650 A | 4/1996 | Leir |
| 5,663,127 A | 9/1997 | Flynn |
| 6,313,335 B1 | 11/2001 | Roberts |
| 6,355,759 B1 | 3/2002 | Sherman |
| 6,511,721 B1 | 1/2003 | Murata |
| 6,923,921 B2 | 8/2005 | Flynn |
| 7,335,786 B1 | 2/2008 | Iyer |
| 7,371,464 B2 * | 5/2008 | Sherman et al. .............. 428/447 |
| 7,501,184 B2 | 3/2009 | Leir |
| 7,745,653 B2 | 6/2010 | Iyer |
| 7,883,652 B2 | 2/2011 | Leir |
| 2007/0148474 A1 | 6/2007 | Leir |
| 2007/0149745 A1 | 6/2007 | Leir |
| 2008/0318057 A1 | 12/2008 | Sherman |
| 2008/0318058 A1 | 12/2008 | Sherman |
| 2011/0092638 A1 | 4/2011 | Leir |
| 2012/0259088 A1 | 10/2012 | Iyer |
| 2012/0264890 A1 | 10/2012 | Hansen |
| 2012/0289736 A1 | 11/2012 | Yang |

FOREIGN PATENT DOCUMENTS

| EP | 1388556 | 2/2004 |
| EP | 2096133 | 9/2009 |
| WO | WO 96/34030 | 10/1996 |
| WO | WO 2004/034139 | 4/2004 |
| WO | WO 2005/003210 | 1/2005 |
| WO | WO 2007/073502 | 6/2007 |
| WO | WO 2007/075317 | 7/2007 |
| WO | WO 2007/075802 | 7/2007 |
| WO | WO 2007/082046 | 7/2007 |

(Continued)

OTHER PUBLICATIONS

De Abajo, "Carbon-13 NMR Sequence Analysis. 23. Synthesis and NMR Spectroscopic Characterization of Polyoxamides with Alternating and Random Sequences of Aliphatic Diamines", Journal of Macromolecular Science, Chemistry, 1984, vol. A21, No. 4, pp. 411-426.

(Continued)

*Primary Examiner* — Mike M Dollinger
(74) *Attorney, Agent, or Firm* — Jean A. Lown

(57) ABSTRACT

A method of preparing polydiorganosiloxane polyoxamide copolymers is described. These copolymers have at least one polydiorganosiloxane segment and at least two aminooxalylamino groups. The method can be used in the presence or absence of a solvent. Intermediates involved in the preparation of the copolymers are also described.

15 Claims, No Drawings

(56) References Cited

FOREIGN PATENT DOCUMENTS

| WO | WO 2008/027594 | 3/2008 |
| WO | WO 2009/002611 | 12/2008 |

OTHER PUBLICATIONS

Gaade, "The Interaction of Diethyl Oxalate and Ethane Diamine", Recueil des Travaux Chimiques des Pays-Bas, Jan. 25, 1936, vol. 55, pp. 325-230.

Gaade, "Esters of Ethane-1 : 2-Dioxamic Acid and Their Derivatives II", Recueil des Travaux Chimiques des Pays-Bas, Jan. 25, 1936, vol. 55, pp. 541-559.

Vogl, "Polyoxamides. I. Preparation and Characterization of Cyclic Oxamides", Macromolecules, Jul.-Aug. 1968, vol. 1, No. 4, pp. 311-315.

International Search Report for PCT/US2010/061817, 3 pages.

\* cited by examiner

METHODS OF MAKING POLYDIORGANOSILOXANE POLYOXAMIDE COPOLYMERS

CROSS REFERENCE TO RELATED APPLICATIONS

This application is a national stage filing under 35 U.S.C. 371 of PCT/US2010/061817, filed Dec. 22, 2010, which claims priority to U.S. Provisional Application No. 61/291,008, filed Dec. 30, 2009, the disclosure of which is incorporated by reference in its/their entirety herein.

TECHNICAL FIELD

Methods of making polydiorganosiloxane polyoxamide copolymers and intermediates useful in the preparation of such copolymers are described.

BACKGROUND

Siloxane polymers have unique properties derived mainly from the physical and chemical characteristics of the siloxane bond. These properties include low glass transition temperature, thermal and oxidative stability, resistance to ultraviolet radiation, low surface energy and hydrophobicity, high permeability to many gases, and biocompatibility. The siloxane polymers, however, often lack tensile strength.

The low tensile strength of the siloxane polymers can be improved by forming block copolymers. Some block copolymers contain a "soft" siloxane (e.g., polydiorganosiloxane) polymeric block or segment and any of a variety of "hard" blocks or segments. Examples include polydiorganosiloxane polyureas and polydiorganosiloxane polyoxamide copolymers. These polymeric materials can be used, for example, to prepare adhesive compositions and various types of polymeric films.

SUMMARY

A method of preparing polydiorganosiloxane polyoxamide copolymers is described. Intermediates involved in the preparation of the copolymers are also described.

In a first aspect, a method of making a polydiorganosilioxane block copolymer is provided. The method includes providing an oxalylamino-containing compound and then reacting the oxalylamino-containing compound with a silicone-based amine. The oxalylamino-containing compound is of Formula (I).

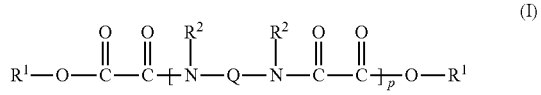

(I)

In this formula, each $R^1$ group is independently an alkyl, haloalkyl, aralkyl, substituted aralkyl, alkenyl, aryl, substituted aryl, or imino of formula $-N=CR^4R^5$.
Each $R^4$ is hydrogen, alkyl, aralkyl, substituted aralkyl, aryl, or substituted aryl. Each $R^5$ is an alkyl, aralkyl, substituted aralkyl, aryl, or substituted aryl. Each $R^2$ is independently hydrogen, alkyl, aralkyl, aryl, or part of a heterocyclic group that includes Q and the nitrogen to which $R^2$ is attached. Group Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and a nitrogen to which $R^2$ is attached, or (e) a combination thereof. The variable p is an integer equal to at least 1. The silicone-based amine that is reacted with the oxalylamino-containing compound has a polydiorganosiloxane segment and at least two primary amino groups, at least two secondary amino groups, or at least one primary amino group plus at least one secondary amino group.

In a second aspect, an oxalylamino-containing compound of Formula (VI) is

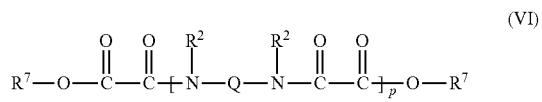

(VI)

In this formula, each $R^7$ is phenyl or a fluorinated alkyl with an alpha-carbon that is non-fluorinated. Each $R^2$ is independently hydrogen, alkyl, aralkyl, aryl, or part of a heterocyclic group that includes Q and a nitrogen to which $R^2$ is attached. Group Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof. The variable p is an integer equal to at least 1.

The above summary is not intended to describe each disclosed embodiment or every implementation of the present invention. The description that follows more particularly exemplifies illustrative embodiments. In several places through the description, guidance is provided through lists of examples, which can be used in various combinations. In each instance, unless stated to the contrary, the recited list serves only as a representative group and should not be interpreted as an exclusive list.

DETAILED DESCRIPTION

A method of preparing polydiorganosiloxane polyoxamide copolymers is described. These copolymers have at least one polydiorganosiloxane segment and at least two aminooxalylamino groups. The method can be used in the presence or absence of a solvent. Intermediates involved in the preparation of the copolymers are also described.

DEFINITIONS

The terms "a", "an", and "the" are used interchangeably with "at least one" to mean one or more of the elements being described.

The term "and/or" means either or both. That is, the expression X and/Y means X, Y or a combination thereof.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, 1-propenyl, and 1-butenyl.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, ethylhexyl, and octadecyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "alkoxy" refers to a monovalent group of formula —OR where R is an alkyl group.

The term "alkoxycarbonyl" refers to a monovalent group of formula —(CO)OR where (CO) denotes a carbonyl group and R is an alkyl group.

The term "aralkyl" refers to a monovalent group of formula —R—Ar where R is an alkylene and Ar is an aryl group. That is, the aralkyl is an alkyl substituted with an aryl. The term "substituted aralkyl" refers to an aralkyl substituted with one or more groups selected from halo, alkyl, haloalkyl, alkoxy, or alkoxycarbonyl. The aryl portion of the aralkyl is typically the group that is substituted.

The term "aralkylene" refers to a divalent group of formula —R—Ar$^a$— where R is an alkylene and Ar$^a$ is an arylene (i.e., an alkylene is bonded to an arylene).

The term "aryl" refers to a monovalent group that is radical of an arene, which is a carbocyclic, aromatic compound. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, naphthyl, acenaphthyl, anthraquinonyl, phenanthryl, anthracenyl, pyrenyl, perylenyl, and fluorenyl. The term "substituted aryl" refers to an aryl substituted with one or more groups selected from halo, alkyl, haloalkyl, alkoxy, or alkoxycarbonyl.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "aryloxy" refers to a monovalent group of formula —OAr where Ar is an aryl group.

The term "carbonyl" refers to a divalent group of formula —(CO)— where the carbon atom is attached to the oxygen atom with a double bond.

The term "carbonylamino" refers to a divalent group of formula —(CO)—NR$^2$— where R$^2$ is hydrogen, alkyl, aryl, aralkyl, or part of a heterocyclic group.

The term "halo" refers to fluoro, chloro, bromo, or iodo.

The term "haloalkyl" refers to an alkyl having at least one hydrogen atom replaced with a halo. Some haloalkyl groups are fluoroalkyl groups, chloroalkyl groups, or bromoalkyl groups.

The term "oxalyl" refers to a divalent group of formula —(CO)—(CO)— where each (CO) denotes a carbonyl group.

The term "oxalylamino" refers to a divalent group of formula —(CO)—(CO)—NR$^2$— where each (CO) denotes a carbonyl group and where R$^2$ is hydrogen, alkyl, aryl, aralkyl, or part of a heterocyclic group.

The term "aminooxalylamino" refers to a divalent group of formula —NR$^2$—(CO)—(CO)—NR$^2$— where each (CO) denotes a carbonyl group and each R$^2$ is hydrogen, alkyl, aryl, aralkyl, or part of a heterocyclic group.

The term "primary amino" refers to a monovalent group —NH$_2$.

The term "secondary amino" refers to a monovalent group —NHR$^3$ where R$^3$ is an alkyl, aryl, aralkyl, or part of a heterocyclic group.

The terms "polymer" and "polymeric material" are used interchangeably and refer to materials prepared from one or more reactants (i.e., monomers). Likewise, the term "polymerize" refers to the process of making a polymeric material from one or more reactants. The terms "copolymer" and "copolymeric material" are used interchangeably and refer to polymeric material prepared from at least two different reactants.

The term "polydiorganosiloxane" refers to a divalent segment of formula

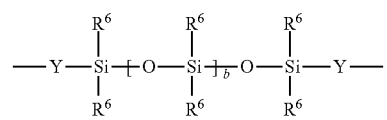

where each R$^6$ is independently an alkyl, haloalkyl, aralkyl, alkenyl, aryl, or substituted aryl; each Y is independently an alkylene, aralkylene, or a combination thereof; and subscript b is independently an integer of 1 to 1500.

The terms "room temperature" and "ambient temperature" are used interchangeably to mean temperatures in the range of 20° C. to 25° C.

Unless otherwise indicated, all numbers expressing feature sizes, amounts, and physical properties used in the specification and claims are to be understood as being modified in all instances by the term "about." Accordingly, unless indicated to the contrary, the numbers set forth are approximations that can vary depending upon the desired properties using the teachings disclosed herein.

The polydiorganosiloxane polyoxamide copolymers are prepared by reacting an oxalylamino-containing compound and a silicone-based amine. The silicone-based amine has at least two amino groups that can react with the oxalylamino-containing compound. More specifically, the silicone-based amine has a polydiorganosiloxane segment and at least two primary amino groups, at least two secondary amino groups, or at least one primary amino group plus at least one secondary amino group. This reaction to form the polydiorganosiloxane polyoxamide copolymers can occur in the presence or absence of an organic solvent.

Other methods of preparing polydiorganosiloxane polyoxamide copolymers have been used in the past. For example, U.S. Pat. No. 7,501,184 (Leir et al.) describes the preparation of these copolymers by first preparing a precursor that contains oxalylamino groups as well as a polydiorganosiloxane segment. That is, the precursor is a silicone-based oxalylamino-containing compound. This precursor is then reacted with an organic amine such as an organic diamine. U.S. Patent Application Publication 2008/0318058 (Sherman et al.) describes the preparation of these copolymers by first preparing a precursor that contains oxalyalmino groups as well as a polyether segment. That is, the precursor is a polyether-based oxalylamino-containing compound. This precursor is then reacted with a silicone-based amine such as a silicone-based diamine having a polydiorganosiloxane segment. Although both of these methods have been used successfully to prepare the copolymers, the methods of making the precursor from a polymeric material typically result in the formation of multiple oxalylamino-containing compounds having different amounts of chain extension. The polymeric precursor is difficult to purify to provide a single compound or a narrower range of molecular weight compounds. In contrast, the method provided herein typically includes the use of precursors that usually have a lower molecular weight than those having a polydiorganosiloxane segment or a polyether segment. If desired, these compounds are more easily purified than the silicone-based oxalylamino-containing compounds or polyether-based oxalylamino-containing compounds. Different batches of copolymer prepared with the current method tend to be more similar to each other than those prepared using the previous methods. That is, the properties (e.g., molecular weight, viscosity, and the like) of the copolymers produced using the current methods tend to be more repeatable from batch to batch.

The oxalylamino-containing compound that is reacted with the silicone-based amine is usually of Formula (I).

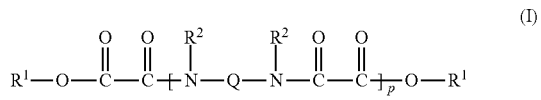
(I)

In Formula (I), each $R^1$ group is independently an alkyl, haloalkyl, aralkyl, substituted aralkyl, alkenyl, aryl, substituted aryl, or imino of formula $-N=CR^4R^5$.
Each $R^4$ is hydrogen, alkyl, aralkyl, substituted aralkyl, aryl, or substituted aryl. Each $R^5$ is an alkyl, aralkyl, substituted aralkyl, aryl, or substituted aryl. Each $R^2$ is independently hydrogen, alkyl, aralkyl, aryl, or part of a heterocyclic group that includes Q and the nitrogen to which $R^2$ is attached (the nitrogen is the heteroatom of the heterocyclic group). Group Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof. The variable p is an integer equal to at least 1.

Suitable alkyl and haloalkyl groups for $R^1$ often have 1 to 10, 1 to 6, or 1 to 4 carbon atoms. Although tertiary alkyl (e.g., tert-butyl) and tertiary haloalkyl groups can be used, a primary or secondary carbon atom is often attached directly (i.e., bonded) to the adjacent oxy group. Exemplary alkyl groups include methyl, ethyl, n-propyl, iso-propyl, n-butyl, and iso-butyl. Exemplary haloalkyl groups include chloroalkyl groups and fluoroalkyl groups in which some, but not all, of the hydrogen atoms on the corresponding alkyl group are replaced with halo atoms. For example, the chloroalkyl or fluoroalkyl groups can be 2-chloroethyl, 2,2,2-trichloroethyl, 3-chloropropyl, 4-chlorobutyl, fluoromethyl, 2-fluoroethyl, 2,2-difluoroethyl, 2,2,2-trifluoroethyl, 1-(trifluoromethyl)-2,2,2-trifluorethyl, 3-fluoropropyl, 4-fluorobutyl, and the like.

Suitable alkenyl groups for $R^1$ often have 2 to 10, 2 to 8, 2 to 6, or 2 to 4 carbon atoms. Exemplary alkenyl groups include ethenyl, propenyl, butenyl, and pentenyl.

Suitable aryl groups for $R^1$ include those having 6 to 12 carbon atoms such as, for example, phenyl. The aryl can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), a haloalkyl (e.g., a haloalkyl having 1 to 4 carbon atoms such as trifluoromethyl), or alkoxycarbonyl (e.g., an alkoxycarbonyl having 2 to 5 carbon atoms such as methoxycarbonyl, ethoxycarbonyl, or propoxycarbonyl).

Suitable aralkyl groups for $R^1$ include those having an alkyl group with 1 to 10 carbon atoms and an aryl group with 6 to 12 carbon atoms. For example, the aralkyl can be an alkyl having 1 to 10 carbon atoms or 1 to 4 carbon atoms substituted with phenyl. The aryl portion of the aralkyl can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), a haloalkyl (e.g., a haloalkyl having 1 to 4 carbon atoms such as trifluoromethyl), or alkoxycarbonyl (e.g., an alkoxycarbonyl having 2 to 5 carbon atoms such as methoxycarbonyl, ethoxycarbonyl, or propoxycarbonyl).

Suitable imino groups for $R^1$ are monovalent groups of formula $-N=CR^4R^5$. Suitable alkyl groups for either $R^4$ or $R^5$ can be linear or branched and typically contain 1 to 10 carbon atoms, 1 to 8 carbon atoms, 1 to 6 carbon atoms, or 1 to 4 carbon atoms. Suitable aryl, substituted aryl, aralkyl, and substituted aralkyl groups for $R^4$ or $R^5$ are the same as those describe above for $R^1$.

Each $R^2$ group in Formula (I) independently can be hydrogen, alkyl, aralkyl, aryl, or part of a heterocyclic group that includes Q and the nitrogen to which $R^2$ is attached. Suitable alkyl groups can be linear or branched and typically contain 1 to 10 carbon atoms, 1 to 8 carbon atoms, 1 to 6 carbon atoms, or 1 to 4 carbon atoms. Suitable aryl groups typically include those having 6 to 12 carbon atoms. The aryl group is often phenyl. Suitable aralkyl groups include those having an alkyl group with 1 to 10 carbon atoms substituted with an aryl group having 6 to 12 carbon atoms. Exemplary aralkyl groups often include an alkyl having 1 to 10 carbon atoms or 1 to 4 carbon atoms substituted with a phenyl. When $R^2$ is part of a heterocyclic group that includes Q and the nitrogen to which $R^2$ is attached, the heterocyclic group typically is saturated or partially saturated and contains at least 4, at least 5, or at least 6 ring members.

Group Q in Formula (I) is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof. Any suitable alkylene can be used for Q. Exemplary alkylene groups often have at least 2 carbon atoms, at least 4 carbon atoms, at least 6 carbon atoms, at least 10 carbon atoms, or at least 20 carbon atoms. Any suitable arylene can be used for Q. Exemplary arylenes often have 6 to 12 carbon atoms and include, but are not limited to, phenylene and biphenylene.

The group Q can be a combination of one or more alkylenes with one or more arylenes. An aralkylene (i.e., a group having an alkylene bonded to an arylene) is a particular combination of one alkylene and one arylene. Other combinations can include, for example, an arylene and two alkylenes such as the group -alkylene-arylene-alkylene-, which can be considered to be an -alkylene-aralkylene- group. In some examples, this group can be of formula $-C_xH_{2x}-C_6H_4-C_xH_{2x}-$ where x is an integer in the range of 1 to 10. One particular example is the group $-CH_2-C_6H_4-CH_2-$.

When group Q includes a carbonylamino group, this group can be of formula $-Q^a-(CO)NR^2-Q^a-$ where each $Q^a$ is independently an alkylene, arylene, or combination thereof. Multiple such groups can be linked such as, for example, $-Q^{3a}-(CO)NR^2-Q^{3a}-(CO)NR^2-Q^{3a}-$ and $-Q^{3a}-(CO)NR^2-Q^{3a}-(CO)NR^2-Q^{3a}-(CO)NR^2-Q^{3a}-$.

Some Q groups combine with both the $R^2$ group and the nitrogen atom to which they are both attached to form a heterocylic group. The heterocylic group often has at least 4, at least 5, or at least 6 ring atoms. The heterocylic group can be unsaturated or partially saturated. One or both of the nitrogen atoms attached to Q can be part of the heterocyclic group. One exemplary heterocyclic group is the divalent group derived from piperizine.

The compound of Formula (I) can be prepared by the condensation reaction of an oxalate of Formula (II) with an organic amine such as an organic diamine of Formula (III) as shown in Reaction Scheme A. The organic diamine of Formula (III) typically does not include a polydiorganosiloxane segment or a perfluoropolyether segment. The organic diamine is typically selected to provide a hard segment for the copolymer.

Reaction Scheme A

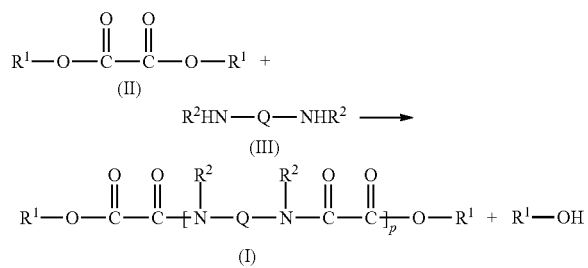

The oxalate that is reacted with the organic amine (e.g., an organic diamine) of Formula (III) is often a compound of Formula (II).

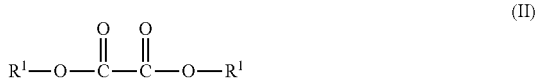

Group $R^1$ is the same as described for Formula (I). The oxalate compound of Formula (II) can be prepared, for example, by reacting a compound of formula $R^1$—OH with oxalyl dichloride. Oxalates of Formula (I) are commercially available (e.g., from Sigma-Aldrich, Milwaukee, Wis. and from VWR International, Bristol, Conn.) and include, but are not limited to, dimethyl oxalate, diethyl oxalate, di-n-butyl oxalate, di-tert-butyl oxalate, and bis(phenyl)oxalate.

In some embodiments, the compounds of Formula (II) have a fluorinated alkyl group for $R^1$. More particularly, the $R^1$ group is a fluorinated alkyl group that is not a perfluoroalkyl group. The fluorinated alkyl often has an alpha-carbon (i.e., the carbon adjacent to the oxy group in Formula (II)) that is non-fluorinated. Suitable groups include, but are not limited to, —$CH_2CF_3$, —$CH_2CHF_2$, —$CH_2CH_2F$, —$CH(CF_3)_2$, and —$CH_2CH_2CH_2F$. Such compounds can be prepared by reacting alcohols such as $CF_3CH_2OH$, $CHF_2CH_2OH$, $CH_2FCH_2OH$, $(CF_3)_2CHOH$, or $CH_2FCH_2CH_2OH$ with oxalyl dichloride. These alcohols are the by-product of the reaction of the resulting oxalate of Formula (II) with the organic amine of Formula (III) to prepare the oxalylamino-containing compounds of Formula (I). Additionally, these alcohols are the by-product of the reaction of the oxalylamino-containing compounds of Formula (I) with a silicone diamine to produce the copolymer of Formula (V) shown below in Reaction Scheme B. These fluorinated alcohols are particularly easily removed from the oxalylamino-containing compounds of Formula (I) and the copolymer of Formula (V).

The product of the reaction can be a single compound having a single value for the variable p or can be a mixture of compounds having multiple values for the variable p. If there is mixture of compounds, various known purification methods can be used to reduce the amount of chain extended material with a value of p greater than 1. Any known purification methods can be used such as, for example, liquid chromatography, recrystallization, distillation, or solvent washing. For example, the compounds with p greater than 1 often are less soluble than those with p equal to 1. The compounds having p values greater than 1 can often be removed by filtration by adding a solvent that dissolves the compounds with p equal to 1 but not the compounds with p greater than 1.

In some embodiment, at least 80 weight percent of the precursor of Formula (I) has a p value equal to 1. The value of p can be controlled, at least partially, by the ratio of components used to prepare the precursor of Formula (I). A large excess of the oxalate compound of Formula (II) (e.g., at least 2 time, at least 3 times, at least 5 times, at least 7 times, or at least 10 times the stoichiometric amount needed to react with the organic amine) tends to favor the formation of precursors where the majority of the compounds have p equal to 1. For example, at least 85 weight percent, at least 90 weight percent, at least 95 weight percent, at least 97 weight percent, at least 98 weight percent, at least 99 weight percent, or at least 99.5 weight percent of the precursor of Formula (I) has a p value equal to 1.

Some exemplary organic diamines of Formula (III) are alkylene diamines (i.e., Q is a alkylene) such as ethylene diamine, propylene diamine, butylene diamine, hexamethylene diamine, 2-methylpentamethylene 1,5-diamine (i.e., commercially available from DuPont, Wilmington, Del. under the trade designation DYTEK A), 1,3-pentane diamine (commercially available from DuPont under the trade designation DYTEK EP), 1,4-cyclohexane diamine, 1,2-cyclohexane diamine (commercially available from DuPont under the trade designation DHC-99), 4,4'-bis(aminocyclohexyl)methane, and 3-aminomethyl-3,5,5-trimethylcyclohexylamine.

Still other exemplary organic diamines of Formula (III) are arylene diamines (i.e., Q is an arylene such as phenylene) such as m-phenylene diamine, o-phenylene diamine, and p-phenylene diamine. Exemplary aralkylene diamines (i.e., Q is an alkylene-arylene group) include, but are not limited to 4-aminomethyl-phenylamine, 3-aminomethyl-phenylamine, and 2-aminomethyl-phenylamine. Exemplary alkylene-aralkylene (i.e., Q is a alkylene-arylene-alkylene group) diamines include, but are not limited to, 4-aminomethyl-benzylamine (i.e, para-xylene diamine), 3-aminomethyl-benzylamine (i.e., meta-xylene diamine), and 2-aminomethyl-benzylamine (i.e., ortho-xylene diamine).

Yet other exemplary diamines have one or more secondary amino groups that are part of a heterocylic group. Examples include, but are not limited to, piperizine.

The condensation reaction shown in Reaction Scheme A between the oxalate compound of Formula (II) and the organic diamine of Formula (III) to produce a compound of Formula (I) can occur in the presence or in the absence of a solvent. In some synthesis methods, no solvent or only a small amount of solvent is included in the reaction mixture. The absence of a solvent can be desirable when the removal of the solvent would be advantageous for the subsequent use of the product of the condensation reaction. In other synthesis methods, a solvent may be included such as, for example, toluene, ethyl acetate, tetrahydrofuran, dichloromethane, alcohols such as ethanol or 2,2,2-trifluoroethanol, 1-methyl-2-pyrrolidinone, or aliphatic hydrocarbons (e.g., alkanes such as hexane).

An excess (based on equivalents) of the oxalate compound of Formula (II) is typically used to form the oxalylamino-containing compound. The excess can be, for example, at least 2 times, at least 3 times, at least 5 times, at least 7 times, or at least 10 times the stoichiometric amount needed to complete the reaction. The excess oxalate compound can typically be removed from the reaction product of the condensation reaction (i.e., compounds of Formulas (I)) using any suitable method. When the product is a solid, a filtration process can be used to remove the excess oxalate. Alternatively, regardless of the physical state of the product, a stripping process can often be used to remove the excess oxalate. For example, the reacted mixture (i.e., the product or products of the condensation reaction) can be heated to a temperature up to 150° C., up to 175° C., up to 200° C., up to 225° C., up to 250° C. or even higher to volatilize the excess oxalate. A vacuum can be pulled to lower the temperature that is needed for removal of the excess oxalate. The compounds of Formula (I) typically undergo minimal or no apparent degradation at temperatures up to 250° C. Any other known methods for removing the oxalate can be used.

The by-product of the condensation reaction is of formula $R^1$—OH (i.e., $R^1$—OH is an alcohol, phenol, or oxime). Group $R^1$ is often selected to produce a by-product $R^1$—OH that can be removed (e.g., vaporized) by heating at temperatures no greater than about 250° C. Such a by-product can be removed when the reacted mixture is heated to remove any excess oxalate compound of Formula (II).

Reaction Scheme B shows the exemplary reaction of the oxalylamino-containing compound of Formula (I) with a silicone-containing diamine of Formula (IV). The divalent $Q^1$ group contains a polydiorganosiloxane segment. The product of the reaction is the copolymer of Formula (V). The by-product of this reaction is the alcohol $R^1$—OH Reaction Scheme B

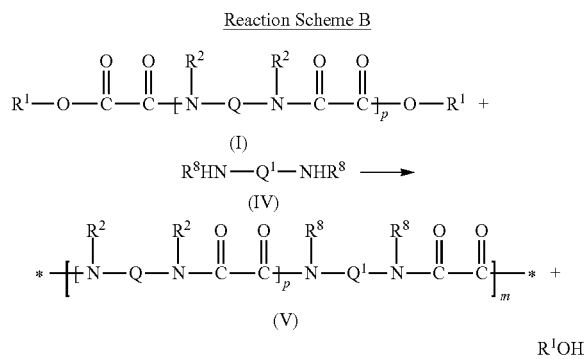

In the copolymer product of Formula (V), m is an integer equal to at least 1, at least 2, at least 3, at least 5, or at least 10. The variable m can be, for example, up to 1000, up to 500, up to 200, up to 100, up to 50, or up to 20. Each p can be equal to at least 1, at least 2, or at least 5. Variable p can be, for example, up to 100, up to 50, up to 20, or up to 10. In some embodiments, the variable p can be in the range of 1 to 20, in the range of 1 to 10, in the range of 1 to 5, in the range of 1 to 3, or in the range of 1 to 2. Each asterisk denotes the attachment to any other group in the copolymer. This other group can be, for example, another group of Formula (V), an end group, or yet another segment in the copolymeric structure.

Any suitable silicone-based amine in Reaction Scheme B can be used provided that the silicone-based amine has at least two primary amino groups, at least two secondary amino groups, or at least one primary amino group plus at least one secondary amino group. The silicone-based amine $R^8$HN-$Q^1$-NHR$^8$ of Formula (IV) is often of Formula (IVa).

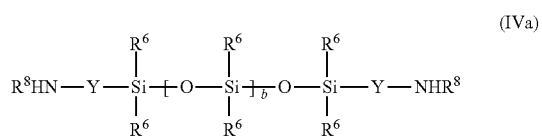

In Formula (IVa), each Y is independently an alkylene, aralkylene, or a combination thereof. Each $R^6$ is independently an alkyl, haloalkyl, aralkyl, substituted aralkyl, alkenyl, aryl, or substituted aryl. Each $R^8$ is independently a hydrogen, alkyl, aryl, or aralkyl. The variable b is an integer greater than equal to 1. The variable b is typically an integer greater than 10, greater than 20, greater than 30, greater than 40. The variable b is often an integer up to 3000, up to 2000, up to 1500, up to 1000, or up to 500. For example, variable b can be in the range of 40 to 1000, 40 to 500, 50 to 500, 50 to 400, 50 to 300, 50 to 200, 50 to 100, 50 to 80, or 50 to 60.

Each $R^8$ group in Formula (IVa) can be independently hydrogen, alkyl, aralkyl, or aryl. Suitable alkyl groups can be linear or branched and typically contain 1 to 10 carbon atoms, 1 to 8 carbon atoms, 1 to 6 carbon atoms, or 1 to 4 carbon atoms. Suitable aryl groups typically include those having 6 to 12 carbon atoms. The aryl group is often phenyl. Suitable aralkyl groups include those having an alkyl group with 1 to 10 carbon atoms substituted with an aryl group having 6 to 12 carbon atoms. Exemplary aralkyl groups often include an alkyl having 1 to 10 carbon atoms or 1 to 4 carbon atoms bonded to a phenyl.

Each group Y in Formula (IVa) is independently an alkylene, aralkylene, or a combination thereof. Suitable alkylene groups typically have up to 10 carbon atoms, up to 8 carbon atoms, up to 6 carbon atoms, or up to 4 carbon atoms. Exemplary alkylene groups include methylene, ethylene, propylene, butylene, and the like. Suitable aralkylene groups usually have an arylene group having 6 to 12 carbon atoms bonded to an alkylene group having 1 to 10 carbon atoms. In some exemplary aralkylene groups, the arylene portion is phenylene. That is, the divalent aralkylene group is phenylene-alkylene where the phenylene is bonded to an alkylene having 1 to 10, 1 to 8, 1 to 6, or 1 to 4 carbon atoms. As used herein with reference to group Y, "a combination thereof" refers to a combination of two or more groups selected from an alkylene and aralkylene group. A combination can be, for example, a single aralkylene bonded to a single alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Suitable alkyl groups for $R^6$ in Formula (IVa) typically have 1 to 10, 1 to 6, or 1 to 4 carbon atoms. Exemplary alkyl groups include, but are not limited to, methyl, ethyl, isopropyl, n-propyl, n-butyl, and iso-butyl. Suitable haloalkyl groups for $R^6$ often have only a portion of the hydrogen atoms of the corresponding alkyl group replaced with a halogen. Exemplary haloalkyl groups include chloroalkyl and fluoroalkyl groups with 1 to 3 halo atoms and 3 to 10 carbon atoms. Suitable alkenyl groups for $R^6$ often have 2 to 10 carbon atoms. Exemplary alkenyl groups often have 2 to 8, 2 to 6, or 2 to 4 carbon atoms such as ethenyl, 1-propenyl, and 1-butenyl. Suitable aryl groups for $R^6$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), a haloalkyl (e.g., a haloalkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), a alkoxycarbonyl (e.g., a alkoxycarbonyl having 1 to 10 carbon atoms, 1 to 6 carbon atoms, or 1 to 4 carbon atoms), or halo (e.g., chloro, bromo, or fluoro). Suitable aralkyl groups for $R^6$ usually have an alkylene group having 1 to 10 carbon atoms and an aryl group having 6 to 12 carbon atoms. In some exemplary aralkyl groups, the aryl group is phenyl and the alkylene group has 1 to 10 carbon atoms, 1 to 6 carbon atoms, or 1 to 4 carbon atoms (i.e., the structure of the aralkyl is alkylene-phenyl where an alkylene is bonded to a phenyl group). The aryl group of the aralkyl can be unsubstituted or substituted with an alkyl (e.g., an alkyl having 1 to 10 carbon atoms, 1 to 6 carbon atoms, or 1 to 4 carbon atoms), a haloalkyl (e.g., a haloalkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), a alkoxycarbonyl (e.g., a alkoxycarbonyl having 1 to 10 carbon atoms, 1 to 6 carbon atoms, or 1 to 4 carbon atoms), or halo (e.g., chloro, bromo, or fluoro).

In many embodiments of Formula (IVa), at least 50 percent of the $R^6$ groups are methyl. For example, at least 60 percent, at least 70 percent, at least 80 percent, at least 90 percent, at least 95 percent, at least 98 percent, at least 99 percent of the $R^6$ groups can be methyl. The remaining $R^6$ groups can be an alkyl having at least two carbon atoms, haloalkyl, aralkyl, substituted aralkyl, alkenyl, aryl, or substituted aryl. In other examples, all of the $R^6$ groups are methyl.

The polydiorganosiloxane diamine of Formula (IVa) can be prepared by any known method and can have any suitable molecular weight, such as an average molecular weight in the range of 700 to 150,000 g/mole. Suitable polydiorganosiloxane diamines and methods of making the polydiorganosiloxane diamines are described, for example, in U.S. Pat. No. 3,890,269 (Martin), U.S. Pat. No. 4,661,577 (Jo Lane et al.), U.S. Pat. No. 5,026,890 (Webb et al.), U.S. Pat. No. 5,276,122 (Aoki et al.), U.S. Pat. No. 5,214,119 (Leir et al.), U.S. Pat. No. 5,461,134 (Leir et al.), U.S. Pat. No. 5,512,650 (Leir et al.), and U.S. Pat. No. 6,355,759 (Sherman et al.). A polydiorganosiloxane diamine having a molecular weight greater than 2,000 g/mole or greater than 5,000 g/mole can be prepared using the methods described in U.S. Pat. No. 5,214,119 (Leir et al.), U.S. Pat. No. 5,461,134 (Leir et al.), and U.S. Pat. No. 5,512,650 (Leir et al.). Some polydiorganosiloxane diamines are commercially available, for example, from Shin Etsu Silicones of America, Inc. (Torrance, Calif.), from Wacker Silicones (Adrian, Mich.), and from Gelest Inc. (Morrisville, Pa.).

In addition to the silicone-based amine, a second amine compound can be included in the reaction mixture to form the copolymer. For example, the second amine can be an organic diamine of Formula (III) described above. In this embodiment, the reaction mixture includes the oxalylamino-containing group of Formula (I), the silicone diamine of Formula (IV), and the organic amine of Formula (III).

Alternatively, the second amine can be an organic amine having more than two primary and/or secondary amino groups. Organic amines having more than two primary and/or secondary amino groups can be used to provide a crosslinked polymeric material. Suitable organic amines having more than two primary and/or secondary amino groups include, but are not limited to, tris(2-aminoethyl)amine, diethylene triamine, triethylene tetraamine, tetraethylene pentamine, and hexaethylene heptamine.

The ratio of equivalents of the oxalylamino-containing compound to equivalents of the silicone-based amine plus any optional second amine compounds that can be used to prepare the copolymer of Formula (V) is often about 1:1. For example the equivalents ratio is often less than or equal to 1:0.90, less than or equal to 1:0.92, less than or equal to 1:0.95, less than or equal to 1:0.98, or less than or equal to 1:1. The equivalents ratio is often greater than or equal to 1:1.02, greater than or equal to 1:1.05, greater than or equal to 1:1.08, or greater than or equal to 1:1.10. For example, the s ratio can be in the range of 1:0.90 to 1:1.10, in the range of 1:0.92 to 1:1.08, in the range of 1:0.95 to 1:1.05, or in the range of 1:0.98 to 1:1.02. Varying the equivalents ratio can be used, for example, to alter the overall molecular weight, which can affect the rheology of the resulting copolymers. Additionally, varying the equivalents ratio can be used to provide oxalylamino-containing end groups or amino end groups, depending upon which reactant is present in excess (based on equivalents).

The condensation reaction of Reaction Scheme B is often conducted at room temperature or at elevated temperatures such as at temperatures up to about 250° C. For example, the reaction often can be conducted at room temperature or at temperatures up to about 100° C. In other examples, the reaction can be conducted at a temperature of at least 100° C., at least 120° C., or at least 150° C. For example, the reaction temperature is often in the range of 100° C. to 220° C., in the range of 120° C. to 220° C., or in the range of 150° C. to 200° C. The condensation reaction is often complete in 1 hour, in 2 hours, in 4 hours, in 8 hours, in 12 hours, in 24 hours, in 36 hours, in 48 hours, in 72 hours, or longer.

Reaction Scheme B can occur in the presence or absence of a solvent. Conducting Reaction Scheme B in the absence of a solvent can be desirable because only the volatile by-product, $R^1OH$ needs to be removed at the conclusion of the reaction. Additionally, a solvent that is not compatible with both reactants and the product can result in incomplete reaction and a low degree of polymerization. In some applications, however, the copolymer will be used in a solvent-based coating composition. In such applications, it can be desirable to prepare the copolymer of Formula (V) in the presence of a solvent.

Suitable solvents usually do not react with any of the reactants or products of the reactions. Additionally, suitable solvents are usually capable of maintaining all the reactants and all of the products in solution throughout the polymerization process. Exemplary solvents include, but are not limited to, toluene, ethyl acetate, tetrahydrofuran, dichloromethane, trifluoroethanol, methyl tert-butyl ether, hexafluoroisopropanol, aliphatic hydrocarbons (e.g., alkanes such as hexane), or mixtures thereof.

Any solvent that is present typically can be stripped from the resulting copolymeric reaction product. Solvents that can be removed under the same conditions used to remove the by-product $R^1$—OH are often preferred. The stripping process is often conducted at a temperature of at least 100° C., at least 125° C., or at least 150° C. The stripping process is typically at a temperature less than 300° C., less than 250° C., or less than 225° C.

Any suitable reactor or process can be used to prepare the copolymeric material according to Reaction Scheme B. The reaction can be conducted using a batch process, semi-batch process, or a continuous process. Exemplary batch processes can be conducted in a reaction vessel equipped with a mechanical stirrer such as a Brabender mixer, which is commercially available from C.W. Brabender Instruments, Inc. (South Hackensack, N.J.), provided the product of the reaction is in a molten state has a sufficiently low viscosity to be drained from the reactor. Exemplary semi-batch process can be conducted in a continuously stirred tube, tank, or fluidized bed. Exemplary continuous processes can be conducted in a single screw or twin screw extruder such as a wiped surface counter-rotating or co-rotating twin screw extruder.

In many processes, the components are metered and then mixed together to form a reaction mixture. The components can be metered volumetrically or gravimetrically using, for example, a gear, piston, or progressing cavity pump. The components can be mixed using any known static or dynamic method such as, for example, static mixers, or compounding mixers such as single or multiple screw extruders. The reaction mixture can then be formed, poured, pumped, coated, injection molded, sprayed, sputtered, atomized, stranded or sheeted, and partially or completely polymerized. The partially or completely polymerized material can then optionally be converted to a particle, droplet, pellet, sphere, strand, ribbon, rod, tube, film, sheet, coextruded film, web, nonwoven, microreplicated structure, or other continuous or discrete shape, prior to the transformation to solid polymer. Any of these steps can be conducted in the presence or absence of applied heat. In one exemplary process, the components can be metered using a gear pump, mixed using a static mixer, and injected into a mold prior to solidification of the polymerizing material.

The polydiorgancsiloxane polyoxamide copolymer of Formula (V) is a linear, block copolymer and can be used as an elastomeric material. These copolymers can be cast from solvents as a film, molded or embossed into various shapes, or extruded into film. The films can be optically clear and can be used in a multilayer film construction. The copolymers can also be formulated into adhesive compositions that can be optically clear.

The polydiorganosiloxane polyoxamide copolymers have both hard segments and soft segments. The soft segments are contributed by the silicone-based amines that have a polydiorganosiloxane segment. In many embodiments, the only soft segments in the copolymer are the polydiorganosiloxane segments. The hard segments are contributed by the oxaylyamido-containing compound and include the Q group.

In another aspect, a compound of Formula (VI) is provided.

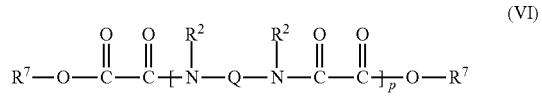
(VI)

In this formula, each $R^7$ is phenyl or a fluorinated alkyl with an alpha-carbon that is non-fluorinated. Each $R^2$ is independently hydrogen, alkyl, aralkyl, aryl, or part of a heterocyclic group that includes Q and the nitrogen to which $R^2$ is attached. Group Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof. The variable p is an integer equal to at least 1.

The groups $R^2$ and Q as well as the variable p are the same as described previously. Group $R^7$ is a phenyl or a fluorinated alkyl with an alpha-carbon that is non-fluorinated. The fluorinated alkyl can be linear or branched and often contains 2 to 10 carbon atoms, 2 to 6 carbon atoms, or 2 to 4 carbon atoms. Examples of $R^7$ include, but are not limited to, —$CH_2CF_3$, —$CH_2CHF_2$, —$CH_2CH_2F$, —$CH(CF_3)_2$, and —$CH_2CH_2CH_2F$.

In some embodiment, at least 80 weight percent of the precursor of Formula (VI) has a p value equal to 1. For example, at least 85 weight percent, at least 90 weight percent, at least 95 weight percent, at least 97 weight percent, at least 98 weight percent, at least 99 weight percent, or at least 99.5 weight percent of the precursor of Formula (I) has a p value equal to 1. The value of p can be controlled, at least partially, by the ratio of components used to prepare the precursor of Formula (VI).

Various items are provided including methods of making a polydiorganosiloxane copolymer and compounds used in the preparation of these copolymers.

A first item is provided that is a method of making a polydiorganosiloxane block copolymer. The method includes providing an oxalylamino-containing compound of Formula (I).

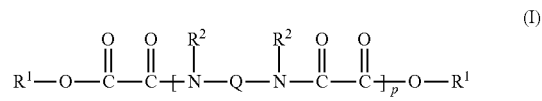
(I)

In Formula (I), each $R^1$ is independently an alkyl, haloalkyl, aralkyl, substituted aralkyl, alkenyl, aryl, substituted aryl, or imino of formula —N=$CR^4R^5$. Each $R^2$ is independently hydrogen, alkyl, aralkyl, aryl, or part of a heterocyclic group that includes Q and a nitrogen to which $R^2$ is attached. Group $R^4$ is hydrogen, alkyl, aralkyl, substituted aralkyl, aryl, or substituted aryl. Group $R^5$ is an alkyl, aralkyl, substituted aralkyl, aryl, or substituted aryl. Group Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof. The variable p is an integer equal to at least 1. The method further includes reacting the oxalylamino-containing compound of Formula (I) with a silicone-based amine, wherein the silicone-based amine has a polydiorganosiloxane segment and at least two primary amino groups, at least two secondary amino groups, or at least one primary amino group plus at least one secondary amino group.

A second item is provided that can be a version of the first item. In the second item, the oxalylamino-containing compound of Formula (I) is prepared by reacting an excess of an oxalate compound of Formula (II)

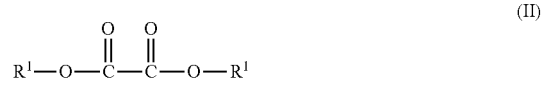
(II)

with an organic diamine of Formula (III).

$R^2HN-Q-NHR^2$ (III)

A third item is provided that can be a version of the first or second item. In the third item, the group $R^1$ is a fluorinated alkyl having an alpha-carbon that is non-fluorinated.

A fourth item is provided that can be a version of any one of the first to third items. In the fourth item, the group $R^1$ is —$CH_2CF_3$, —$CH_2CH_2F$, —$CH_2CHF_2$, —$CH(CF_3)_2$ or —$CH_2CH_2CH_2F$.

A fifth item is provided that can be a version of the first or second items. In the fifth item, the group $R^1$ is phenyl.

A sixth item is provided that can be a version of any one of the first to fifth items. In the sixth item, the silicone-based amine is of Formula (IVa).

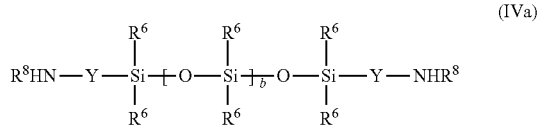

(IVa)

In Formula (IVa), each Y is independently an alkylene, aralkylene, or a combination thereof. Each $R^6$ is independently an alkyl, haloalkyl, aralkyl, substituted aralkyl, alkenyl, aryl, or substituted aryl. Each $R^8$ is independently hydrogen, alkyl, aralkyl, or aryl. The variable b is an integer greater than or equal to 1.

A seventh item is provided that can be a version of any one of the first to sixth items. In the seventh item, at least 80 weight percent of the oxalylamino-containing compound of Formula (I) has p equal to 1.

An eighth item is provided that can be a version of any one of the first to seventh items. In the eighth item, at least 98 weight percent of the oxalylamino-containing compound of Formula (I) has p equal to 1.

A ninth item is provided that is a compound of Formula (V).

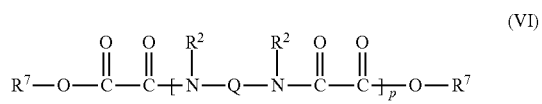

(VI)

In Formula (VI), each $R^7$ is phenyl or a fluorinated alkyl with an alpha-carbon that is non-fluorinated. Each $R^2$ is independently hydrogen, alkyl, aralkyl, aryl, or part of a heterocyclic group that includes Q and a nitrogen to which $R^2$ is attached. Group Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof. The variable p is an integer equal to at least 1.

A tenth item is provided that can be a version of the ninth item. In the tenth item, group $R^7$ is —$CH_2CF_3$, —$CH_2CH_2F$, —$CH_2CHF_2$, —$CH(CF_3)_2$ or —$CH_2CH_2CH_2F$.

An eleventh item is provided that can be a version of the ninth item. In the eleventh item, group $R^7$ is phenyl.

A twelfth item is provided that can be a version of any one of the ninth to eleventh items. In the twelfth item, at least 80 weight percent of the oxalylamino-containing compound of Formula (VI) has p equal to 1.

A thirteenth item is provided that can be a version of any one of the ninth to twelfth items. In the thirteenth item, at least 98 weight percent of the oxalylamino-containing compound of Formula (VI) has p equal to 1.

EXAMPLES

Solvents and other reagents used were obtained from Sigma-Aldrich Chemical Company, Milwaukee, Wis. or EMD Chemicals, Gibbstown, N.J. unless otherwise noted.

| Table of Materials | |
|---|---|
| Component | Description |
| PDMS diamine | A polydimethylsiloxane diamine of the following formula. |
| | $H_2N$—〜〜—Si(CH$_3$)$_2$—[O—Si(CH$_3$)$_2$]$_n$—O—Si(CH$_3$)$_2$—〜〜—$NH_2$ |
| | PDMS diamine with a number average molecular weight of about 1,000 grams/mole or 10,000 grams/mole were purchased from Wacker Chemical Company (Adrian, MI). PDMS diamines with a number average molecular weight of about 5,000 grams/mole, about 20,000 grams/mole, about 25,000 grams/mole, and about 35,000 grams/mole can be prepared according to the procedure described in Example 2 of U.S. Pat. No. 5,214,119. |
| MTBE | Methyl tert-butyl ether obtained from EMD Chemicals (Gibbstown, NJ) |
| EtOAc | Ethyl acetate obtained from EMD Chemicals (Gibbstown, NJ) |
| NMP | 1-methyl-2-pyrrolidinone obtained from Alfa Aesar (Ward Hill, MA) |
| $CHCl_3$ | Chloroform obtained from EMD Chemicals (Gibbstown, NJ) |
| $CH_2Cl_2$ | Dichloromethane obtained from EMD Chemicals (Gibbstown, NJ) |
| Hexanes | Solvent obtained from EMD Chemicals (Gibbstown, NJ) |
| Heptane | Solvent obtained from EMD Chemicals (Gibbstown, NJ) |
| Toluene | Solvent obtained from EMD Chemicals (Gibbstown, NJ) |
| THF | Tetrahydrofuran obtained from EMD Chemicals (Gibbstown, NJ) |
| Trifluoroethanol | 2,2,2-trifluoroethanol obtained from Halocarbon (River Edge, NJ) |

-continued

Table of Materials

| Component | Description |
|---|---|
| MeOH | Methanol obtained from EMD Chemicals (Gibbstown, NJ) |
| Ethanol | 200 proof alcohol obtained from Koptec (King of Prussia, PA) |
| Component | Description |
| DYTEK A | 2-methyl-1,5-pentanediamine obtained from DuPont (Wilmington, DE) |
| EDR-148 | Ethylene glycol bis(2-aminoethyl) ether obtained from Huntsman (The Woodlands, TX) |
| XDA | m-xylylene diamine obtained from TCI America (Portland, OR) |
| EDA | 1,2-diaminoethane obtained from Sigma-Aldrich Chemical Company (Milwaukee, WI) |
| BDA | 1,4-diaminobutane obtained from Sigma-Aldrich Chemical Company (Milwaukee, WI) |
| HMDA | Hexamethylene diamine obtained from Alfa Aesar (Ward Hill, MA) |
| Piperazine | Organic amine obtained from Sigma-Aldrich Chemical Company (Milwaukee, WI) |
| Pyridine | Organic amine obtained from Sigma-Aldrich Chemical Company (Milwaukee, WI) |
| Oxalyl chloride | Reactant obtained from Sigma-Aldrich Chemical Company (Milwaukee, WI) |
| Diethyl oxalate | Reactant obtained from Alfa Aesar (Ward Hill, MA) |
| Diphenyl oxalate | Reactant obtained from TCI America (Portland, OR) |
| Ambient temperature | Refers to a temperature in the range of about 20 to 25° C.; used interchangeably with the term "room temperature" |

Test Methods

Titration Method to Determine Amine Equivalent Weight (AEW) of PDMS Diamines

The amine equivalent weight (AEW) of PDMS diamines was determined in tetrahydrofuran (THF) using standardized HCl (1N) and titrating to a bromophenol blue endpoint.

Inherent Viscosity (IV)

Inherent viscosity measurements were carried out at 27° C. on a LAUDA PVS 1 viscosity system obtained from Lauda-Brinkman (Delran, N.J.) utilizing size 50 capillary viscometers (Part #9721-A00) from Cannon Instrument Company (State College, Pa.) in a THF solution at a concentration of 0.2 grams/deciliter and are reported in units of deciliters/gram (dL/g).

Preparatory Example P1

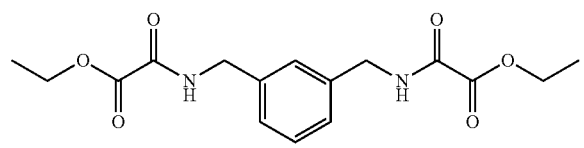 [SMILES: CCOC(=O)C(=O)NCc1cccc(CNC(=O)C(=O)OCC)c1]

A solution of XDA (25 grams) in ethanol (50 mL) was added dropwise to an ice-cooled solution of diethyl oxalate (268 grams) in ethanol (500 mL) over 15 minutes, maintaining the internal temperature below 6° C. The ice bath was removed, and after 20 hours, the cloudy reaction mixture was filtered through a pad of diatomaceous earth filtering media commercially available under the trade designation CELITE from World Minerals (Santa Barbara, Calif.). The volatiles were removed from the filtrate, first on a rotary evaporator, then by means of a mechanical vacuum pump while maintaining a subsurface argon sparge and heating in a 150° C. oil bath. The resulting m-xylyl-bis-oxamic acid ethyl ester was obtained as a clear, viscous resin. $^1$H NMR (CDCl$_3$, 300 MHz) δ 7.43 (brs, 2H), 7.35-7.30 (m, 1H), 7.25-7.22 (m, 3H), 4.50 (d, J=6 Hz, 4H), 4.34 (q, J=7 Hz 4H), 1.38 (t, J=7 Hz, 6H).

Preparatory Example P2

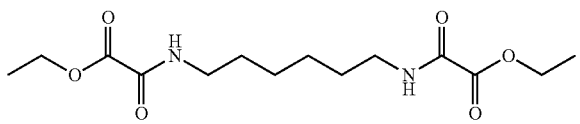 [SMILES: CCOC(=O)C(=O)NCCCCCCNC(=O)C(=O)OCC]

The method of Example II in U.S. Pat. No. 2,343,808 was used. Molten HMDA (27.1 grams) was poured into a solution of diethyl oxalate (136 grams) in ethanol (127 mL) and stirred for 18 hours. The solid was collected by filtration, dissolved in CH$_2$Cl$_2$ (150 mL) and purified by flash column chromatography (EtOAc as the eluent). The resulting solid was boiled in MTBE (150 mL), cooled to ambient temperature, and then collected by filtration to obtain 19.8 grams of hexamethylene-bis-oxamic acid ethyl ester as white needles having a melting point in the range of 91.6 to 92.5° C. $^1$H NMR (CDCl$_3$, 300 MHz) δ 7.13 (brs, 2H), 4.34 (q, J=7.2 Hz, 4H), 3.33 (q, J=6.9 Hz, 4H), 1.59-1.52 (m, 4H), 1.37 (t, J=7.2 Hz, 6H), 1.39-1.34 (m, 4H).

Preparatory Example P3

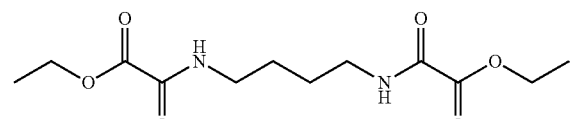

A solution of 1,4-diaminobutane (88.2 grams) in 100 mL ethanol was added to ice cooled diethyl oxalate (1461 grams) in ethanol (1400 mL) over 40 minutes, maintaining the internal temperature below 8° C. The reaction was allowed to gradually warm to ambient temperature, and after 48 hours, the crude solids (168 grams) were collected by filtration. The product (22 grams) was purified by flash column chromatography (EtOAc as the eluent) and then boiled in MTBE (200 mL) to obtain butylene-bis-oxamic acid ethyl ester as a white solid having a melting point in the range of 114.4 to 116.4° C. $^{1}$H NMR (CDCl$_{3}$, 300 MHz) δ 7.23 (brs, 2H), 4.33 (q, J=7.1 Hz, 4H), 3.36 (q, J=6.5 Hz, 4H), 1.64-1.59 (m, 4H), 1.36 (t, J=7.2 Hz, 6H).

Preparatory Example P4

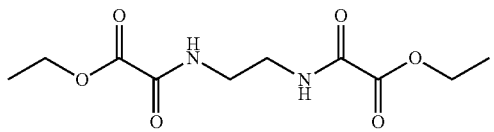 [SMILES: CCOC(=O)C(=O)NCCNC(=O)C(=O)OCC]

Ethylene-bis-oxamic acid ethyl ester was prepared and purified according to the procedure of Preparatory Example P3 using EDA as the diamine. The reaction mixture contained EDA (25 grams) and diethyl oxalate (602 grams) to afford the product as white crystals having a melting point in the range of 129.9 to 130.6° C. $^{1}$H NMR (CDCl$_{3}$, 300 MHz) δ 7.61 (brs, 2H), 4.34 (q, J=7.2 Hz, 4H), 3.57-3.55 (m, 4H), 1.37 (t, J=7.2 Hz, 6H).

Preparatory Example P5

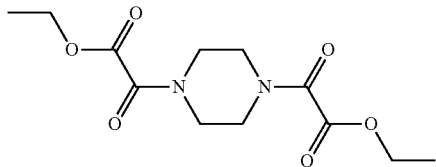 [SMILES: CCOC(=O)C(=O)N1CCN(C(=O)C(=O)OCC)CC1]

Piperazine (15 grams) and diethyl oxalate (150 grams) were added to a 16 ounce jar, and the mixture was gently heated by placing the jar in a bath of warm water to dissolve the solids. After cooling to ambient temperature, the jar was placed in an oven at 60° C. for 2 hours, cooled to ambient temperature, and a small amount of insoluble solid was removed by filtration. MTBE (200 mL) was added to the filtrate, and after standing in a refrigerator at 4° C. for 18 hours, the product was collected by filtration to obtain 30.1 grams of piperazine-bis-oxamic acid ethyl ester as a white solid having a melting point in the range of 122.3 to 123.3° C. $^{1}$H NMR (CDCl$_{3}$, 300 MHz) δ 4.39-4.30 (m, 4H), 3.72-3.68 (m, 4H), 3.53-3.49 (m, 4H), 1.37 (dt, J$_{j}$=7.2 Hz, J$_{2}$=2.5 Hz, 6H).

Preparatory Example P6

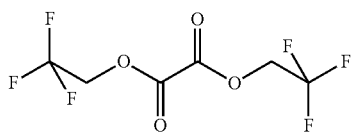 [SMILES: O=C(OCC(F)(F)F)C(=O)OCC(F)(F)F]

A 3 liter 3-neck round bottom flask equipped with mechanical stirrer, addition funnel, temperature probe, and nitrogen inlet was charged with 2,2,2-trifluoroethanol (500 grams), methyl tert-butyl ether (1300 mL), and pyridine (593 grams). The contents were cooled using an ice bath, and oxalyl chloride (317 grams) was added dropwise over 1 hour, maintaining the internal temperature below 2° C. The reaction mixture was allowed to warm to ambient temperature, it was stirred for 2 hours, and then the solids were removed by filtration. The filtrate was washed twice with 1 liter of cold 1N HCl, once with 1 liter of cold water, and once with 300 mL of 15 weight percent sodium carbonate solution. The organic layer was dried over anhydrous sodium sulfate and then concentrated on a rotary evaporator. The resulting oil was distilled at atmospheric pressure, and the fraction boiling in the range of 159 to 163° C. was collected to obtain 245 grams of 2,2,2-trifluoroethyl oxalate as a clear, colorless oil.

Example 1

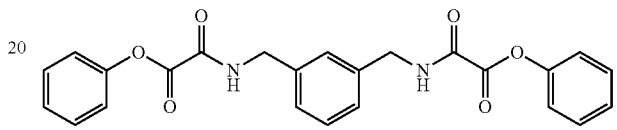

A solution of XDA (2.72 grams) in NMP (50 mL) was added to a solution of diphenyl oxalate (48.4 grams) in NMP (200 mL) over 1 hour at ambient temperature. The reaction mixture was stirred for 18 hours, after which time it was poured into 1 liter of ice water. The resulting solid was collected by filtration, and a portion was dissolved in CHCl$_{3}$ and purified by flash column chromatography (40 volume percent EtOAc in hexanes to 75 volume percent EtOAc in hexanes as the eluent) followed by recrystallization from MeOH to afford m-xylyl-bis-oxamic acid phenyl ester as white crystals having a melting point in the range of 136.7 to 137.5° C. $^{1}$H NMR (CDCl$_{3}$, 300 MHz) δ 7.52 (brs, 2H), 7.45-7.36 (m, 5H), 7.32-7.26 (m, 5H), 7.20-7.15 (m, 4H), 4.59 (d, J=6.2 Hz, 4H).

Example 2

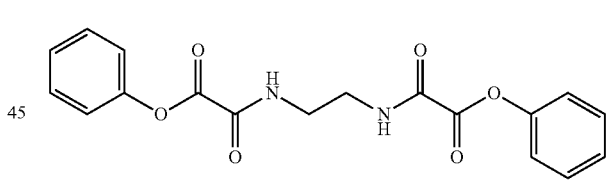

A solution of EDA (1.202 grams) in NMP (50 mL) was added to an ice-cooled solution of diphenyl oxalate (48.4 grams) in NMP (200 mL) over 25 min. The ice bath was removed, the reaction was stirred for 1 hour, and then the solid was collected by filtration. It was washed with water and dried to obtain ethylene-bis-oxamic acid phenyl ester as a white solid. $^{1}$H NMR (d$_{6}$-DMSO, 300 MHz) δ 9.28 (s, 2H), 7.48-7.24 (m, 10H), 3.40 (s, 4H).

Example 3

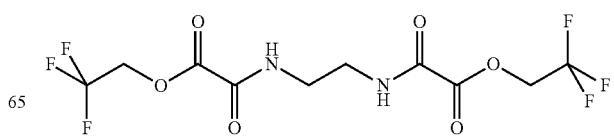

A 500 mL 3-neck round bottom flask equipped with a magnetic stirbar, thermocouple, and argon inlet was charged with 2,2,2-trifluoroethyl oxalate (from Preparatory Example P7) (152.5 grams) and 2,2,2-trifluoroethanol (150 grams). The contents were cooled in an ice bath, and a mixture of ethylene diamine (EDA) (3.606 grans) in 2,2,2-trifluoroethanol (40 grams) was added dropwise over a period of 75 minutes. The cooling bath was removed, and the contents were stirred for 18 hours, after which time methyl tert-butyl ether (100 mL) was added, and the solids were then collected via filtration. The resulting 10.2 grams of solids was recrystallized from boiling 2,2,2-trifluoroethanol (416 grams) to obtain 9.23 grams of ethylene-bis-oxamic acid trifluoroethyl ester as white crystals having a melting point of 223° C. $^1$H NMR (300 MHz, $d_6$-DMSO) δ 9.18 (brs, 2H), 4.92 (q, J=8.9 Hz, 4H), 3.31-3.29 (m, 4H).

Example 4

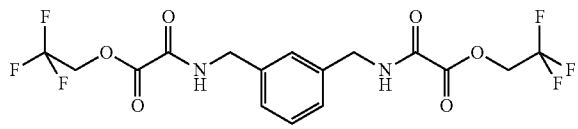 [SMILES: O=C(NCc1cccc(CNC(=O)C(=O)OCC(F)(F)F)c1)C(=O)OCC(F)(F)F]

A 1 liter jacketed resin kettle with mechanical stirrer, argon inlet, thermocouple, and addition funnel was charged with 2,2,2-trifluoroethyl oxalate (266 grams) and 2,2,2-trifluoroethanol (388 grams). The contents were cooled to −20° C. by means of a recirculating chiller. A solution of XDA (12.8 grams) in 2,2,2-trifluoroethanol (128 grams) was added over 20 minutes, the reaction temperature was then increased to 0° C., and then the volatiles were removed on a rotary evaporator to afford a white solid. The solid was briefly boiled in MTBE and then collected by filtration to obtain 36.4 grams of crude material. A portion of this material (15.9 grams) was dissolved in a 50/50 mixture of EtOAc/heptane (v/v) and filtered to remove a small amount of insoluble material. The filtrate was partially concentrated on a rotary evaporator, and the product was collected by filtration and dried in a vacuum oven at 85° C. for 15 hours to afford 15.32 grams of m-xylyl-bis-oxamic acid trifluoroethyl ester as a white solid having a melting point in the range of 103.3 to 104.2° C. $^1$H NMR (300 MHz, $d_6$-DMSO) δ 9.62 (t, J=5.8 Hz, 2H), 7.32-7.27 (m, 1H), 7.22-7.17 (m, 3H), 4.92 (q, J=8.9 Hz, 4H), 4.34 (d, J=6.2 Hz, 4H).

Example 5

A 1 liter resin kettle was charged with a PDMS diamine (amine equivalent weight equal to 12,397 grams/mole, 450 grams) and m-xylyl-bis-oxamic acid ethyl ester (from Preparatory Example P1) (6.10 grams). The mixture was heated to 150° C. and stirred under a $N_2$ atmosphere for 20 hours. During this time, the viscosity got much higher, and the material went from milky to clear in appearance. The polymer was poured out and allowed to stand at room temperature to afford a clear, tough, colorless rubber slab (IV equal to 1.378 dL/g).

Example 6

A vial was charged with a PDMS diamine (amine equivalent weight equal to 501 grams/mole, 10.0 grams) and m-xylyl-bis-oxamic acid ethyl ester (from Preparatory Example P1) (3.36 grams). The vial was capped and shaken to afford an unmovable mass. It was placed in an oven at 150° C. until melted, then shaken again and allowed to cool to form a stiff rubber.

Example 7

A 1 liter resin kettle was charged with a PDMS diamine (amine equivalent weight equal to 5365 grams/mole, 211 grams) and m-xylyl-bis-oxamic acid ethyl ester (from Preparatory Example P1) (6.61 grams). The mixture was heated to 150° C. and stirred under a $N_2$ atmosphere for 70 hours. During this time, the viscosity got much higher, and the material went from milky to nearly clear but slightly hazy in appearance. The polymer was poured out and allowed to stand at room temperature to afford a nearly clear, slightly hazy, tough, colorless rubber slab (IV equal to 0.794 dL/g).

Example 8

A 1 liter resin kettle was charged with a PDMS diamine (amine equivalent weight equal to 12,397 grams/mole, 400 grams) and butylene-bis-oxamic acid ethyl ester (from Preparatory Example P3) (4.70 grams). The mixture was heated to 150° C. and stirred under a $N_2$ atmosphere for 18 hours. During this time, the viscosity got much higher, and the material went from milky to nearly clear but slightly hazy in appearance. The polymer was poured out and allowed to stand at room temperature to afford a nearly clear, slightly hazy, tough, colorless rubber slab (IV equal to 1.014 dL/g).

Example 9

A 4 ounce jar was charged with PDMS diamine (amine equivalent weight equal to 12,644 grams/mole, 14.6 grans), m-xylyl-bis-oxamic acid phenyl ester (from Example 1) (250 milligrams), and $CHCl_3$ (15 grams) and then placed on a roller for 18 hours. The material was diluted with additional $CHCl_3$, transferred to a Teflon tray, dried under ambient conditions for 18 hours, and finally in a vacuum oven at 90° C. for 2.5 hours to afford a clear elastomer (IV equal to 1.635 dL/g).

Example 10

A 500 mL 3-neck round bottom flask was charged with PDMS diamine (amine equivalent weight equal to 12,644 grams/mole, 252.9 grams) and ethylene-bis-oxamic acid ethyl ester (from Preparatory Example P4) (2.603 grams). The mixture was heated to 150° C. and stirred under a $N_2$ atmosphere for 45 hours. During this time, the viscosity got much higher, and the material went from milky to clear in appearance. The polymer was poured out and allowed to stand at room temperature to afford a clear, tough, colorless rubber slab (IV equal to 0.948 dL/g).

Example 11

A 40 mL vial was charged with ethylene-bis-oxamic acid trifluoroethyl ester (from Example 3) (105.0 mg), PDMS diamine (amine equivalent weight equal to 16,911 g/mol, 9.645 grams), and THF (20.0 grams), and the vial was placed on a roller for 5 days. The clear, viscous solution was poured into a Teflon tray, and the solvent was allowed to evaporate at ambient conditions for 18 hours, and then in a vacuum oven at 150° C. for 2 hours to afford a clear, tough elastomer (IV equal to 1.879 dL/g).

Example 12

A 2 liter resin kettle was charged with ethylene-bis-oxamic acid trifluoroethyl ester (from Example 3) (3.7491 grams), PDMS diamine (amine equivalent weight equal to 10,174 grams/mole, 207.19 grams), and toluene (1036 grams). The reaction mixture was stirred under an argon atmosphere at 85° C. for 16 hours, then at 105° C. for 24 hours. The resulting clear, viscous reaction mixture was poured into a Teflon tray. The solvent was removed in an oven at 125° C. to afford a clear, tough elastomer (IV equal to 1.909 dL/g).

Example 13

A 2 liter resin kettle was charged with m-xylyl-bis-oxamic acid trifluoroethyl ester (from Example 4) (8.7305 grams), PDMS diamine (amine equivalent weight equal to 10,174 grams/mole, 399.84 grams), and EtOAc (933 grams). The reaction mixture was stirred under an argon atmosphere at 55° C. for 22 hours and then cooled to ambient temperature. A portion of the clear, viscous solution was dried in a Teflon tray at 65° C. for 27 hours followed by additional drying in a vacuum oven at 100° C. for 1 hour to afford a clear, tough elastomer (IV equal to 2.293 dL/g).

Example 14

A 40 mL vial was charged with m-xylyl-bis-oxamic acid trifluoroethyl ester (from Example 4) (785.3 mg), PDMS diamine (amine equivalent weight equal to 2548 grams/mole, 9.007 grams), and EtOAc (21.0 grams). The vial was placed in a Launder-O-Meter (available from Atlas Electric Devices Co., Chicago, Ill.) at 60° C. for 17.5 hours, at which time the contents were cooled to ambient temperature, poured into a Teflon tray, and dried in an oven at 80° C. for 1 hour and 100° C. for 2 hours to afford a clear, colorless elastomer (IV equal to 0.957 dL/g).

Example 15

A master batch was prepared from PDMS diamine (amine equivalent weight equal to 17,526 grams/mole, 235.14 grams), EtOAc (560 grams), and Dytek A (390 mg). Based on a titration of this mixture, the amine concentration was 0.02532 milliequivalents/gram. This master batch (183.51 grams) was placed in an 8 ounce jar, followed by m-xylyl-bis-oxamic acid trifluoroethyl ester (from Example 4) (1.032 g), and the jar was placed on a roller for 3 days. The slightly hazy, viscous mixture was transferred to a Teflon tray, and the solvent was removed in an oven at 80° C. for 2 hours and then at 100° C. for 3 hours to afford a clear, colorless elastomer.

We claim:

1. A method of making a polydiorganosiloxane block copolymer, the method comprising:
   providing an oxalylamino-containing compound of Formula (I)

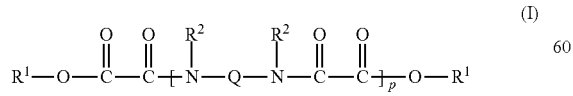

wherein
   each $R^1$ is independently an alkyl, haloalkyl, aralkyl, substituted aralkyl, alkenyl, aryl, substituted aryl, or imino of formula $-N=CR^4R^5$;
   each $R^2$ is independently hydrogen, alkyl, aralkyl, aryl, or part of a heterocyclic group that includes Q and a nitrogen to which $R^2$ is attached;
   $R^4$ is hydrogen, alkyl, aralkyl, substituted aralkyl, aryl, or substituted aryl;
   $R^5$ is an alkyl, aralkyl, substituted aralkyl, aryl, or substituted aryl;
   Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof;
   p is an integer equal to at least 1 and wherein at least 90 weight percent of the compound of Formula (I) has p equal to 1; and
   reacting the oxalylamino-containing compound of Formula (I) with a silicone-based amine,
   wherein the silicone-based amine has a polydiorganosiloxane segment and at least two primary amino groups, at least two secondary amino groups, or at least one primary amino group plus at least one secondary amino group.

2. The method of claim 1, wherein the oxalylamino-containing compound of Formula (I) is prepared by reacting an excess of an oxalate compound of Formula (II)

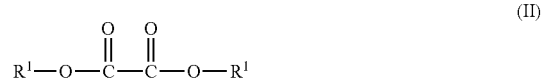

with an organic diamine of Formula (III)

3. The method of claim 1, wherein $R^1$ is a fluorinated alkyl having an alpha-carbon that is non-fluorinated.

4. The method of claim 1, wherein $R^1$ is $-CH_2CF_3$, $-CH_2CH_2F$, $-CH_2CHF_2$, $-CH(CF_3)_2$, or $-CH_2CH_2CH_2F$.

5. The method of claim 1, wherein $R^1$ is phenyl.

6. The method of claim 1, wherein the silicone-based amine is of Formula (IVa)

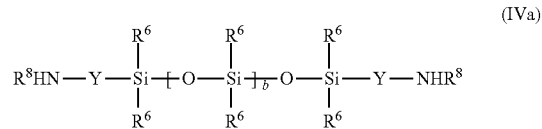

wherein
   each Y is independently an alkylene, aralkylene, or a combination thereof;
   each $R^6$ is independently an alkyl, haloalkyl, aralkyl, substituted aralkyl, alkenyl, aryl, or substituted aryl;
   each $R^8$ is independently hydrogen, alkyl, aralkyl, aryl, and
   b is an integer greater than or equal to 1.

7. The method of claim 1, wherein at least 95 weight percent of the oxalylamino-containing compound of Formula (I) has p equal to 1.

8. The method of claim 1, wherein at least 98 weight percent of the oxalylamino-containing compound of Formula (I) has p equal to 1.

9. A compound of Formula (VI)

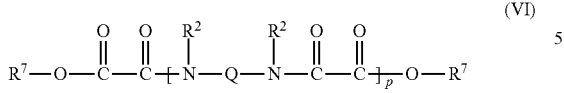
(VI)

wherein
each $R^7$ is a fluorinated alkyl with an alpha-carbon that is non-fluorinated;
each $R^2$ is independently hydrogen, alkyl, aralkyl, aryl, or part of a heterocyclic group that includes Q and a nitrogen to which $R^2$ is attached;
Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof; and
p is equal to 1.

10. The compound of claim 9, wherein $R^7$ is $-CH_2CF_3$, $-CH_2CH_2F$, $-CH_2CHF_2$, $-CH(CF_3)_2$, or $-CH_2CH_2CH_2F$.

11. A method of making a polydiorganosiloxane block copolymer, the method comprising:
a) providing mixture of oxalylamino-containing compounds of Formula (I) having different values of p

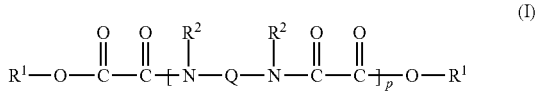
(I)

wherein
each $R^1$ is independently an alkyl, haloalkyl, aralkyl, substituted aralkyl, alkenyl, aryl, substituted aryl, or imino of formula $-N=CR^4R^5$;
each $R^2$ is independently hydrogen, alkyl, aralkyl, aryl, or part of a heterocyclic group that includes Q and a nitrogen to which $R^2$ is attached;
$R^4$ is hydrogen, alkyl, aralkyl, substituted aralkyl, aryl, or substituted aryl;
$R^5$ is an alkyl, aralkyl, substituted aralkyl, aryl, or substituted aryl;
Q is (a) an alkylene, (b) arylene, (c) a carbonylamino group linking a first group to a second group, wherein the first group and the second group are each independently an alkylene, arylene, or a combination thereof, (d) part of a heterocyclic group that includes $R^2$ and the nitrogen to which $R^2$ is attached, or (e) a combination thereof;
p is an integer equal to at least 1; and
b) purifying the mixture of oxalylamino-containing compounds to prepare a precursor wherein at least 90 weight percent of the oxalylamino-containing compounds in the precursor are of Formula (I) where p is equal to 1; and
c) reacting the precursor with a silicone-based amine, wherein the silicone-based amine has a polydiorganosiloxane segment and at least two primary amino groups, at least two secondary amino groups, or at least one primary amino group plus at least one secondary amino group.

12. The method of claim 11, wherein the mixture of oxalylamino-containing compounds of Formula (I) are prepared by reacting an excess of an oxalate compound of Formula (II)

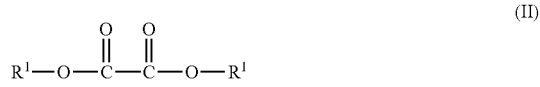
(II)

with an organic diamine of Formula (III)

(III).

13. The method of claim 11, wherein the silicone-based amine is of Formula (IVa)

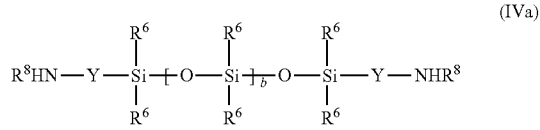
(IVa)

wherein
each Y is independently an alkylene, aralkylene, or a combination thereof;
each $R^6$ is independently an alkyl, haloalkyl, aralkyl, substituted aralkyl, alkenyl, aryl, or substituted aryl;
each $R^8$ is independently hydrogen, alkyl, aralkyl, aryl, and
b is an integer greater than or equal to 1.

14. The method of claim 11, wherein at least 95 weight percent of the oxalylamino-containing compounds in the precursor are of Formula (I) where p is equal to 1.

15. The method of claim 11, wherein at least 98 weight percent of the oxalylamino-containing compounds in the precursor are of Formula (I) where p is equal to 1.

* * * * *

UNITED STATES PATENT AND TRADEMARK OFFICE
CERTIFICATE OF CORRECTION

PATENT NO. : 8,765,881 B2
APPLICATION NO. : 13/514497
DATED : July 1, 2014
INVENTOR(S) : David Hays It is certified that error appears in the above-identified patent and that said Letters Patent is hereby corrected as shown below:

In the Specification

<u>Column 1</u>
Lines 44-45, delete "polydiorganosilioxane" and insert -- polydiorganosiloxane --, therefor.

<u>Column 2</u>
Line 11, delete "is" and insert -- is provided. --, therefor.

<u>Column 4</u>
Line 61, delete "oxalyalmino" and insert -- oxalylamino --, therefor.

<u>Column 9</u>
Line 43 (Approx.), delete "$R^1$—OH" and insert -- $R^1$—OH. --, therefor.

<u>Column 13</u>
Line 36, delete "polydiorgancsiloxane" and insert -- polydiorganosiloxane --, therefor.

Lines 49-50, delete "oxaylyamido" and insert -- oxalylamido --, therefor.

<u>Column 19</u>
Line 52, delete "$J_j$" and insert -- $J_1$ --, therefor.

<u>Column 22</u>
Line 36, delete "grans)," and insert -- grams), --, therefor.

Signed and Sealed this
Twenty-first Day of October, 2014

Michelle K. Lee
*Deputy Director of the United States Patent and Trademark Office*